(12) United States Patent
Schraut et al.

(10) Patent No.: US 10,266,477 B2
(45) Date of Patent: *Apr. 23, 2019

(54) METHOD FOR PRODUCING DIESTERS OF TEREPHTHALIC ACID WITH ENRICHMENT OF RECIRCULATED ALCOHOL

(71) Applicant: BASF SE, Ludwigshafen (DE)

(72) Inventors: Armin Schraut, Bensheim (DE); Martin Kaller, Mannheim (DE); Rob Bronneberg, Wattenheim (DE); Jasmin Stammer, Freinsheim (DE); Martin Das, Mannheim (DE); Gerrit Harnischmacher, Mannheim (DE)

(73) Assignee: BASF SE (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/513,775

(22) PCT Filed: Sep. 21, 2015

(86) PCT No.: PCT/EP2015/071578
§ 371 (c)(1),
(2) Date: Mar. 23, 2017

(87) PCT Pub. No.: WO2016/046120
PCT Pub. Date: Mar. 31, 2016

(65) Prior Publication Data
US 2017/0297998 A1    Oct. 19, 2017

(30) Foreign Application Priority Data

Sep. 24, 2014 (EP) .................................. 14186137
Feb. 2, 2015 (EP) .................................. 15153483

(51) Int. Cl.
*C07C 67/08* (2006.01)
*B01D 3/36* (2006.01)
*B01J 19/00* (2006.01)
*C07C 67/58* (2006.01)

(52) U.S. Cl.
CPC ............... *C07C 67/08* (2013.01); *B01D 3/36* (2013.01); *B01J 19/0013* (2013.01); *B01J 19/0066* (2013.01); *C07C 67/58* (2013.01); *B01J 2219/00094* (2013.01)

(58) Field of Classification Search
None
See application file for complete search history.

(56) References Cited

U.S. PATENT DOCUMENTS

| | | | |
|---|---|---|---|
| 2,825,738 A | 3/1958 | Ellendt et al. | |
| 4,372,857 A | 2/1983 | Matthews et al. | |
| 4,407,662 A | 10/1983 | Ginder | |
| 5,792,651 A | 8/1998 | Colpan et al. | |
| 6,699,386 B2 | 3/2004 | Todokoro et al. | |
| 6,916,950 B2 | 7/2005 | Gubisch et al. | |
| 7,276,621 B2 | 10/2007 | Cook | |
| 7,385,075 B2 | 6/2008 | Disteldorf et al. | |
| 7,714,111 B2 | 5/2010 | Sun et al. | |
| 7,799,942 B2 | 9/2010 | Osborne et al. | |
| 8,034,970 B2 * | 10/2011 | Hassan ............... B01F 7/00766 560/76 |
| 8,729,292 B2 | 5/2014 | Friese | |
| 9,260,373 B2 | 2/2016 | Disteldorf et al. | |
| 2007/0161815 A1 | 7/2007 | Osborne et al. | |
| 2008/0139760 A1 | 6/2008 | DeBruin | |
| 2011/0251420 A1 | 10/2011 | Disteldorf et al. | |
| 2014/0148612 A1 | 5/2014 | De Munck et al. | |
| 2016/0264509 A1 | 9/2016 | Kaller et al. | |
| 2017/0044085 A1 | 2/2017 | Kaller et al. | |

FOREIGN PATENT DOCUMENTS

| | | |
|---|---|---|
| EP | 142157 A2 | 5/1985 |
| EP | 158754 A1 | 10/1985 |
| EP | 205582 A1 | 12/1986 |
| EP | 233692 A1 | 8/1987 |
| EP | 0407037 B1 | 1/1991 |
| EP | 1186593 A2 | 3/2002 |

(Continued)

OTHER PUBLICATIONS

English Translation of International Preliminary Report on Patentability for International Application No. PCT/EP2015/071578, dated Jan. 11, 2017.
U.S. Appl. No. 15/513,757, filed Mar. 23, 2017.
International Preliminary Examination Report with Applicant's Response (in German) for PCT/EP2015/071576 dated Dec. 7, 2016.
International Search Report for PCT/EP2015/071574 dated Dec. 17, 2015.
International Search Report for PCT/EP2015/071576 dated Dec. 17, 2015.
International Search Report for PCT/EP2015/071578 dated Dec. 21, 2015.

(Continued)

*Primary Examiner* — Ana Z Muresan
(74) *Attorney, Agent, or Firm* — Drinker Biddle & Reath LLP

(57) ABSTRACT

The present invention relates to a process for preparing a terephthalic diester by reacting terephthalic acid with at least one alcohol, wherein terephthalic acid is suspended in the alcohol in a dispersing tank, the preliminary suspension is passed from the dispersing tank into a reactor and converted in the presence of an esterification catalyst, and water of reaction is distilled off together with the vapor as alcohol-water azeotrope, the vapor is at least partly condensed, the condensate is separated into an aqueous phase and an organic phase and the organic phase is conducted through a column in which the organic phase is run counter to at least a portion of the vapor, and the organic phase is collected in the lower region of the column and at least partly passed into the dispersing tank.

23 Claims, 1 Drawing Sheet

(56) References Cited

FOREIGN PATENT DOCUMENTS

| | | |
|---|---|---|
| FR | 2719039 A1 | 10/1995 |
| GB | 2088739 A | 6/1982 |
| GB | 2151501 A | 7/1985 |
| JP | H04308543 A | 10/1992 |
| JP | 2007077041 A | 3/2007 |
| JP | 49564945 | 6/2012 |
| WO | WO-8603686 A1 | 7/1986 |
| WO | WO-9521178 A1 | 8/1995 |
| WO | WO-99063076 A1 | 12/1999 |
| WO | WO-2005003152 A1 | 1/2005 |
| WO | WO-2005111059 A2 | 11/2005 |
| WO | WO-2007115046 A1 | 10/2007 |
| WO | WO-2010076192 A1 | 7/2010 |
| WO | WO-2010076193 A1 | 7/2010 |
| WO | WO-2012025308 A1 | 3/2012 |

OTHER PUBLICATIONS

International Search Report for PCT/EP2015/071579 dated Jan. 8, 2016.
Written Opinion of the International Searching Authority for PCT/EP2015/071574 dated Dec. 17, 2015.
Written Opinion of the International Searching Authority for PCT/EP2015/071578 dated Dec. 21, 2015.
Written Opinion of the International Searching Authority for PCT/EP2015/071579 dated Jan. 8, 2016.
U.S. Appl. No. 15/513,730, filed Mar. 23, 2017.
U.S. Appl. No. 15/513,716, filed Mar. 23, 2017.

\* cited by examiner

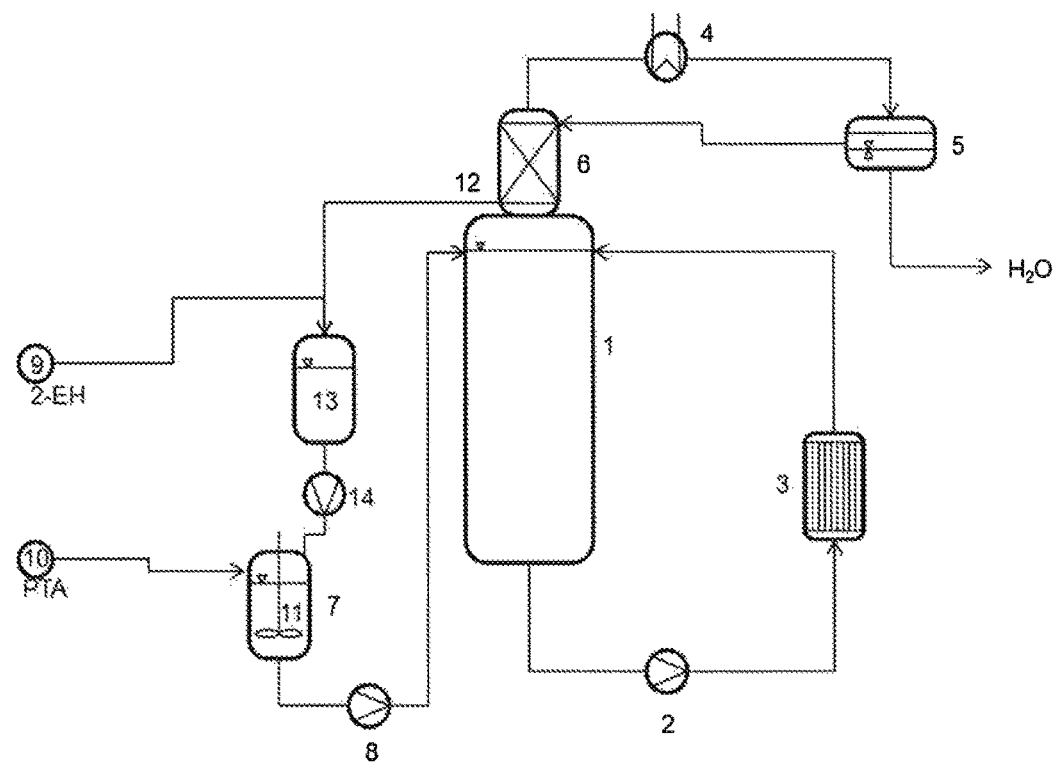

METHOD FOR PRODUCING DIESTERS OF TEREPHTHALIC ACID WITH ENRICHMENT OF RECIRCULATED ALCOHOL

CROSS-REFERENCE TO RELATED APPLICATIONS

This application is a national stage application (under 35 U.S.C. § 371) of PCT/EP2015/071578, filed Sep. 21, 2015, which claims benefit of European Application Nos. 14186137.7, filed Sep. 24, 2014, and 15153483.1, filed Feb. 2, 2015, all of which are incorporated herein by reference in their entirety.

The invention relates to a process for preparing terephthalic diesters by reacting terephthalic acid with at least one alcohol.

Esters of terephthalic acid find use as plasticizers and are notable for favorable toxicological properties.

It is known that carboxylic esters can be prepared by reacting carboxylic acids with alcohols. This reaction can be conducted autocatalytically or catalytically, for example by means of Brønsted or Lewis acids. Irrespective of the manner of catalysis, the result is always a temperature-dependent equilibrium between the feedstocks (carboxylic acid and alcohol) and the products (ester and water).

In order to shift the equilibrium in favor of the ester (or of the full ester in the case of polybasic acids), an azeotroping agent is generally used, which helps to remove the water of reaction from the mixture. If one of the feedstocks (alcohol or carboxylic acid) has a lower boiling point than the ester formed and forms a miscibility gap with water, it is possible to use a reactant as azeotroping agent and recycle it back into the mixture after water has been removed. In the case of esterification of higher aliphatic carboxylic acids, aromatic carboxylic acids or di- or polybasic carboxylic acids, the alcohol used is generally the azeotroping agent.

If the alcohol used serves as azeotroping agent, the procedure is typically to at least partly condense the vapor from the reactor, to separate the condensate into an aqueous phase and an organic phase consisting essentially of the alcohol used for the esterification, and to recycle the organic phase at least partly into the reactor.

EP-A 1 186 593 describes a process for preparing carboxylic esters by reacting di- or polycarboxylic acids or anhydrides thereof with alcohols, wherein the water of reaction is removed by azeotropic distillation with the alcohol. The amount of liquid removed from the reaction by the azeotropic distillation is made up again completely or partly by the alcohol.

WO 2010/076192 A1 proposes removing low boilers from the organic phase to be recycled in order to prevent the accumulation thereof in the reactor system.

U.S. Pat. No. 7,276,621 B2 describes a process for titanate-catalyzed esterification of terephthalic acid with 2-ethylhexanol. An inert gas is passed through the reaction mixture in order to promote the removal of water.

JP 4956945 B2 also describes a process for esterification of terephthalic acid with 2-ethylhexanol. In this case, the terephthalic acid is introduced into the reaction system continuously or batchwise as a slurry. The metered addition is effected at the same rate at which the terephthalic acid is converted to the product.

U.S. Pat. No. 7,799,942 B2 describes a process for preparing terephthalic diesters in a reactor at atmospheric pressure using a distillation column atop the reactor. In addition, an inert gas flows through the reaction mixture.

U.S. Pat. No. 7,385,075 B2 describes a process for preparing esters of polybasic $C_4$-$C_{10}$ carboxylic acids and $C_3$-$C_8$ alcohols by heating in the presence of a catalyst. The vapor is separated by rectification into an alcohol-rich phase and a water-rich phase. The alcohol-rich phase is recycled into the reaction mixture; the water-rich phase is condensed and at least part is discharged.

WO 2010/076193 A1 describes a process for purifying the crude ester product of an esterification reaction, in which a metallic esterification catalyst is used.

US 2014/0148612 A1 describes a process for preparing esters, in which a mixture of an acid or anhydride with an excess of alcohol is brought to reaction temperature by supplying energy, with initial throttling of the energy supply in order to avoid foam formation, and the energy supply can subsequently be increased.

The solubility of terephthalic acid in higher alcohols is low. For example, terephthalic acid is soluble in 2-ethylhexanol at 180° C. only to an extent of less than 0.65% by weight. The reaction of terephthalic acid with higher alcohols proceeds only via the proportion of terephthalic acid present dissolved in the alcohol. For the attainment of high conversions, it is essential to ensure constant mixing of the heterogeneous mixture of terephthalic acid and alcohol, and effective introduction of heat into the reaction system. In addition, it is important to keep the water content in the reaction mixture low, in order to be able to shift the reaction equilibrium to the product side and, if hydrolysis-sensitive esterification catalysts are used, to prevent the hydrolysis of the catalyst. The metered addition of solid terephthalic acid into the reactor containing boiling alcohol, for example via a conveying screw, in which the powder drops into the reactor in freefall at the free end of the screw, is possible only with difficulty because of the risk of the terephthalic acid forming lumps. In the case of tall reactors of high volume, the arrangement of a reservoir vessel for solid terephthalic acid above the reactor is often associated with construction difficulties.

It is therefore an object of the invention to provide a process for preparing terephthalic diesters which allows simple introduction of the terephthalic acid into the reactor and achieves full conversion of the terephthalic acid. It is a further object of the invention to provide a process which can be performed in existing reactors for esterification reactions through minor retrofitting.

The present invention therefore provides a process for preparing a terephthalic diester by reacting terephthalic acid with at least one alcohol, wherein)
a) terephthalic acid is suspended in the alcohol in a dispersing tank to obtain a preliminary suspension,
b) the preliminary suspension is passed from the dispersing tank into a reactor and converted in the presence of an esterification catalyst, and
c) water of reaction is distilled off together with the vapor as alcohol-water azeotrope, the vapor is at least partly condensed, the condensate is separated into an aqueous phase and an organic phase and the organic phase is conducted through a column in which the organic phase is run counter to at least a portion of the vapor, and the organic phase is collected in the lower region of the column and at least partly passed into the dispersing tank and/or intermediately stored in a collecting vessel and passed out of the collecting vessel into the dispersing tank for the same batch or a subsequent batch.

A BRIEF DESCRIPTION OF THE FIGURE

FIG. 1 shows a plant suitable for performing the process according to the invention.

The process according to the invention can be performed batchwise or continuously, but is preferably performed batchwise.

The process gets around the problems associated with the metered addition of solid terephthalic acid into the reactor, such as formation of terephthalic acid lumps and blockage of the conveying screw or another conveying unit. The process provides for the preparation of a preliminary suspension in a dispersing tank. Terephthalic acid is metered into the reactor not in solid form but in the form of a suspension.

The preliminary suspension is prepared by suspending pulverulent terephthalic acid in a portion or the total amount of the alcohol in the dispersing tank. For this purpose, a suitable mixing apparatus is used. For instance, an amount of the terephthalic acid can be mixed with alcohol using a stirrer; alternatively, dispersing pumps can be used. For example, the total amount of terephthalic acid can be suspended in one step, or the terephthalic acid can be suspended in portions over the course of the process. For the suspension in portions, it is possible to meter terephthalic acid into the dispersing tank, for example, with the aid of a conveying screw.

The mixing can also be effected in a closed chamber through the interaction of a rotating rotor and a stator, in which case only an incremental amount of the components is continuously mixed together in each case, and the suspension then leaves the chamber.

The alcohol used to prepare the preliminary suspension is at least partly return alcohol, i.e. the organic phase which is obtained after condensation of the vapor, phase separation of the condensate and collection of the organic phase of the condensate conducted through a column in the lower region of the column. For the initial provision of the preliminary suspension for starting up the process, it is possible to use fresh alcohol, for example 4- 50% of the total amount of the alcohol, preferably 5- 40% of the total amount of the alcohol.

The dispersing tank usually consists of metallic materials, preference being given to stainless steel. The dispersing tank can be connected to the reactor on the gas side.

The preliminary suspension is passed into the reactor using a pump or by means of gravity. Usable pumps are in principle all the conveying pumps known to those skilled in the art that are regarded as suitable in view of the properties of the preliminary suspension to be conveyed. Conveying pumps usable with preference are a centrifugal pump, piston pump, screw pump, impeller pump or peristaltic pump. The preliminary suspension can be metered into the reactor in portions or continuously. The metered addition is preferably effected continuously. The preliminary suspension can in principle be metered in at any point in the reactor, but preference is given to adding the preliminary suspension in the upper region of the reactor, especially above the liquid level in the reactor. In this way, backflow counter to the direction of metered addition can very substantially be prevented.

The reactor may be any reactor suitable for performance of chemical reactions in the liquid phase. Suitable reactors are non-backmixed reactors such as tubular reactors or delay vessels provided with internals, but preferably backmixed reactors such as stirred tanks, loop reactors, jet loop reactors or jet nozzle reactors. Optionally, it is also possible to combine a plurality of reactors in a multistage apparatus. Reactors of this kind are, for example, loop reactors with installed sieve trays, cascaded vessels, tubular reactors with intermediate feeding or stirred columns.

Preference is given to using a stirred tank reactor. Stirred tank reactors usually consist of metallic materials, preference being given to stainless steel.

Especially preferred is the use of existing reaction systems which are utilized, for example, for the esterification of phthalic anhydride and can be used for the esterification of terephthalic acid through minor retrofitting. Retrofitting operations are necessary, relating particularly to the provision of a dispersing tank and of a lateral draw in the column for diverting the organic phase into the dispersing tank.

In the reactor, the preliminary suspension and the esterification catalyst are brought into contact, which gives a reaction suspension. In one embodiment of the process, i) the preliminary suspension is passed into the unfilled reactor, ii) the preliminary suspension is heated to boiling and iii) the esterification catalyst is added. Optionally, the sequence of steps ii) and iii) can be reversed.

In one embodiment of the process, the esterification catalyst is initially charged in the reactor in a portion of alcohol, for example 4-50% of the total amount of alcohol, preferably 5-40%. The catalyst/alcohol mixture can first be heated to boiling and then the metered addition of the preliminary suspension can be started. Alternatively, the preliminary suspension is added to the catalyst/alcohol mixture and then heated. Optionally, the heating of the catalyst/alcohol mixture and the metered addition of the preliminary suspension can be performed in parallel. Alternatively, the catalyst is preferably metered into the preliminary suspension which has been heated to boiling in the reactor.

Particular preference is given to a process in which
b1) the reactor is initially charged with a mixture of alcohol and catalyst having a temperature at or above the boiling temperature of the alcohol and at or above the minimum reaction temperature, and
b2) the preliminary suspension is metered into the reactor.

The minimum reaction temperature is regarded as the temperature from which the reaction between terephthalic acid and alcohol proceeds spontaneously in the presence of the catalyst and a reaction pressure. With the metered addition of the preliminary suspension, the reaction starts promptly. The reaction rate and hence the formation rate of water of reaction can be controlled via the rate of metered addition of the preliminary suspension. In this way, unwanted foaming of the reaction mixture can be prevented, for example, by slowing the feed of the preliminary suspension without having to throttle the energy input into the reaction mixture. The control of the reaction rate via the rate of metered addition of the preliminary suspension allows rapid response behavior, whereas control via the energy input allows only a retarded response.

It is preferable in the interests of a short cycle time that the heating of the initially charged mixture of alcohol and catalyst is effected with maximum energy input. It is additionally preferable that the energy input is not throttled on commencement of the metered addition of the preliminary suspension.

The mixture of alcohol and catalyst initially charged in the reactor is suitably prepared by initially charging alcohol, heating it to boiling and adding the catalyst. It is preferable in the interests of a short setup time that the heating of the initially charged alcohol is effected at maximum energy input.

The preliminary suspension has, for example, a concentration of 1 to 50 g, preferably 10 to 40 g, of terephthalic acid per 100 g of preliminary suspension. The preliminary suspension is suitably metered in at a rate of 0.1 to 0.8 start volume per hour, the start volume being regarded as the volume of the mixture of alcohol and catalyst initially charged in the reactor.

In general, the preliminary suspension is metered into the reactor at a temperature above ambient temperature, preferably at a temperature of 50 to 150° C., for example 100 to 130° C. The return alcohol used in accordance with the invention to prepare the preliminary suspension is obtained at a temperature sufficient to heat the preliminary suspension to, for example, 50 to 150° C. The initially prepared preliminary suspension can optionally be heated externally.

During the reaction, the reaction suspension in the reactor has a temperature close to the boiling point of the reaction mixture, for example a temperature of 150° C. to 250° C., preferably of 185° C. to 220° C. The boiling point of the reaction suspension is dependent on the ratio of terephthalic diester to alcohol and rises over the course of the reaction.

The heating of the initially charged alcohol, the preliminary suspension and/or a catalyst/alcohol mixture in the reactor can be effected in any desired manner, for example using a heating medium in a jacketed vessel, pipelines or ducts through which a heating medium flows and which are connected to the reactor wall in a heat-conducting manner, by electrical heating, by pumped circulation of the initially charged mixture through an external heat exchanger or by means of an internal heating register which is heated using a heating medium such as steam or oil. For example, heating can be accomplished using welded-on half-coils, i.e. pipe segments in the shape of a half-shell, laid around the reactor and welded to the reactor wall.

Heat can be introduced into the reaction system in the same way. Preference is given to heating the reaction suspension by pumping it in circulation through a heat exchanger positioned outside the reactor. Useful heat exchangers in principle include all the known heat exchangers, for example plate heat exchangers or shell and tube heat exchangers, or combinations thereof.

Appropriately, the reaction suspension is drawn off from the reactor using a pump and passed through the heat exchanger. The heat exchanger is connected to the reactor in a fluid-conducting manner for the recycling of the heated reaction suspension into the reactor. The reaction suspension can in principle be drawn off at various positions in the reactor below the liquid level of the reaction suspension, but the reaction suspension is preferably drawn off at the lowest point in the reactor. In this case, the reactor is configured such that the reaction suspension is drawn off at the geodetically lowest point in the reactor, and there are no dead spaces caused by locally lowest points in the reactor. The pump for drawing off the reaction suspension may in principle be disposed at various positions outside the reactor. For example, the pump is disposed at the geodetically lowest point in the circuit consisting of reactor, pump and connecting lines.

Suitable pumps are in principle all the conveying pumps known to those skilled in the art that are regarded as suitable for performing the process according to the invention in view of the properties of the reaction suspension to be conveyed, usable. Conveying pumps usable with preference are a centrifugal pump, piston pump, screw pump, impeller pump or peristaltic pump. Very particular preference is given to an axial or radial centrifugal pump.

The reaction suspension can in principle be recycled into the reactor at any position in the reactor, but it is appropriately recycled in the upper region of the reactor, for example at the height of the liquid level of the reaction suspension or in the range from the height of the liquid level of the reactor suspension to 30% below it. The volume flow rate which is conducted through the heating device is chosen, for example, such that the complete reactor contents are circulated within a period of 1 to 60 minutes, preferably 1 to 10 minutes. The constant circulation of the reactor contents assures effective mixing of the reaction suspension.

Optionally, the mixing of the reaction suspension can be promoted by the metered addition of an inert gas into the reactor, especially at the lowest point in the reactor, and/or a stream of the reaction suspension. Especially in the event of disrupted operation of the pump for the drawing-off of the reaction suspension, for example in the event of failure of the pump, the metered addition of the inert gas contributes to preventing sedimentation of terephthalic acid at the base of the reactor or in pipelines. Preferably, the inert gas is metered in on the suction side of the pump. Alternatively, the metered addition can be effected on the pressure side of the pump or simultaneously on the suction side and pressure side. This enables maintenance of the circulation through the heat exchanger even if the pump fails. Inert gases are all gases which do not have any reactivity with the constituents of the reaction suspension under the reaction conditions, especially nitrogen or argon. Preferably, the inert gas is metered into the reactor in an amount of 0.01 to 5 units by volume of the inert gas per unit by volume of the reaction suspension per hour. The metered addition of the inert gas can optionally also be utilized for recirculation of the reactor contents.

Alternatively or additionally, the mixing can be promoted by the use of a stirrer.

During the reaction, an alcohol-water mixture is distilled off together with the vapor, the vapor is at least partly condensed, the condensate is separated into an aqueous phase and an organic phase and the organic phase is conducted through a column in which the organic phase is run counter to at least a portion of the vapor, and the organic phase is collected in the lower region of the column and at least partly passed into the dispersing tank. Alternatively or additionally, the organic phase collected in the lower region of the column can be intermediately stored in a collecting vessel and passed out of the collecting vessel into the dispersing tank for the same batch or a subsequent batch.

Condensation or partial condensation of the vapor can be effected using any suitable condensers. These can be cooled with any desired cooling media. Condensers with air cooling and/or water cooling are preferred, and air cooling is particularly preferred.

The condensate obtained is subjected to a phase separation into an aqueous phase and an organic phase. For this purpose, the condensate is typically passed into a phase separator (decanter), where it divides into two phases as a result of mechanical settling, and these can be drawn off separately. The aqueous phase is removed and, optionally after workup, can be discarded or used as stripping water in the aftertreatment of the ester.

The organic phase is conducted through a column (called return alcohol column) in which the recycled organic phase is run counter to at least a portion of the vapor. The return alcohol column may, for example, be a tray column, column with structured packing or column with random packing. A small number of plates is generally sufficient. A suitable example is a column having 2 to 10 theoretical plates. Preferably, the column is placed atop the reactor, i.e. connected directly to the reactor. Appropriately, the organic phase is introduced into the return alcohol column at the top or in the upper region. In the lower region of the column, the descending condensate of the return alcohol column is collected. For this purpose, a collecting tray is suitably provided in the lower region of the column, for example a chimney tray with homogeneously distributed roofed chimneys. The collecting tray has, for example, an inward gradient and a central collecting cup and collecting stub. From the collecting tray of the column, the collected condensate is passed as return alcohol into the dispersing tank. Instead of passing the return alcohol directly into the dispersing tank, the return alcohol can also be intermediately stored in a collecting vessel. It is thus possible to balance out variations between the occurrence of the return alcohol and the requirement of alcohol for production of the preliminary suspension. Appropriately, the return alcohol is passed from the collecting vessel into the dispersing tank when fresh alcohol is required in the dispersing tank for the production of the preliminary suspension. The return alcohol is available for the making-up of the preliminary suspension for a current batch, but also for a subsequent batch. The return alcohol can be led off by means of gravity or using a conveying device, for example a centrifugal pump, piston pump, screw pump, impeller pump or circulation pump.

The recycling of the organic phase via the return alcohol column has the advantage that the recycled organic phase is depleted of traces of water which have remained in the organic phase after the phase separation or are dissolved in the organic phase in accordance with their thermodynamic solubility. The water content in the recycled organic phase which is at least partly passed into the dispersing vessel is less than the maximum solubility of water in the alcohol, preferably less than 3% by weight, especially less than 0.5% by weight.

The return alcohol which has been passed into the dispersing tank is available for the suspension of terephthalic acid in the dispersing tank. The metered addition of the terephthalic acid as a preliminary suspension can be effected in a distribution over the reaction time. This dispenses with the requirement for handling of concentrated preliminary suspensions. This has the advantage that the suspension supplied to the reactor has a low solids content and hence can be conveyed efficiently. In addition, the use of return alcohol means that the concentration of solids in the reactor is likewise low, which allows optimal utilization of the reaction volume. A further advantage is that fewer problems occur as a result of sedimentation in the event of failure of the circulation pump.

In the process according to the invention, preference is given to using linear, branched or cyclic aliphatic alcohols having 4 to 18 carbon atoms, especially 8 to 14 carbon atoms, or aromatic alcohols. The alcohols are monools and/or polyols and may be tertiary, secondary or primary.

The alcohols used may originate from various sources. Suitable feedstocks are, for example, fatty alcohols, alcohols from the Alfol process, or alcohols or alcohol mixtures which have been obtained by hydrogenating saturated or unsaturated aldehydes, especially those whose synthesis includes a hydroformylation step.

Aliphatic alcohols which are used in the process according to the invention are, for example, n-butanol, isobutanol, pentanols, hexanols, heptanols, octanols such as n-octanol, 2-ethylhexanol, nonanols, decyl alcohols or tridecanols, prepared by hydroformylation or aldol condensation and subsequent hydrogenation. The alcohols can be used as a pure compound, as a mixture of isomeric compounds or as a mixture of compounds having different numbers of carbon atoms. One example of such an alcohol mixture is a $C_9/C_{11}$ alcohol mixture.

Aromatic alcohols which can be used in the process according to the invention are, for example, phenol, benzyl alcohol, 1-naphthol, 2-naphthol, 1,2-dihydroxybenzene, 1,3-dihydroxybenzene, 1,4-dihydroxybenzene, 1,4-naphthohydroquinone, 2,4,6-trinitrophenol, primary phenylethyl alcohol, secondary phenylethyl alcohol, phenylpropyl alcohol, o-tolyl alcohol, p-tolyl alcohol, cuminic alcohol, p-nitrophenol, m-, o- or p-alkylphenol, e.g. m-, o- or p-methylphenol or m-, o- or p-ethylphenol,
m-, o- or p-halophenol, e.g. m-, o- or p-chlorophenol or m-, o- or p-bromophenol. In addition, it is possible to use p-nitrobenzyl alcohol, m-, o- or p-alkylbenzyl alcohol, e.g. m-, o- or p-methylbenzyl alcohol or m-, o- or p-ethylbenzyl alcohol,
m-, o- or p-halobenzyl alcohol, e.g. m-, o- or p-chlorobenzyl alcohol or m-, o- or p-bromobenzyl alcohol, 2-ethoxyphenol, 3-ethoxyphenol, 4-ethoxyphenol, 2-propoxyphenol, 3-propoxyphenol, 4-propoxyphenol, 2-ethoxybenzyl alcohol, 3-ethoxybenzyl alcohol, 4-ethoxybenzyl alcohol, 2-propoxybenzyl alcohol, 3-propoxybenzyl alcohol or 4-propoxybenzyl alcohol.

Polyols which can be used in the process according to the invention are, for example, propane-1,2-diol, propane-1,3-diol, butane-1,2-diol, butane-1,3-diol, butane-1,4-diol, neopentyl glycol, pentane-1,5-diol, hexane-1,6-diol, decane-1,10-diol, diethylene glycol, 2,2,4-trimethylpentane-1,5-diol, 2,2-dimethylpropane-1,3-diol, 1,4-dimethylolcyclohexane, 1,6-dimethylolcyclohexane, glycerol, trimethylolpropane, erythritol, pentaerythritol and sorbitol.

Particularly preferred alcohols are 2-ethylhexanol, 2-propylheptanol, isononanol isomer mixtures, decanol isomer mixtures and $C_9/C_{11}$ alcohol mixtures.

The alcohol to be converted, which serves as azeotroping agent, can be used in a stoichiometric excess. Preferably, the amount of alcohol used is selected such that a mixture of ester and unconverted alcohol comprising 10% to 35% by weight of alcohol would be obtained in the case of theoretical full conversion of the terephthalic acid.

In the real performance of the process, the ester may become concentrated, especially when, with advanced conversion, the condensed vapor is no longer recycled completely into the reactor. The actual amount of alcohol in the crude product of the conversion may be 1% to 15% by weight, for example 5% to 12% by weight.

The inventive esterification is conducted in the presence of an esterification catalyst.

In a preferred embodiment of the process according to the invention, the esterification catalyst is soluble in the alcohol.

The esterification catalyst is suitably selected from Lewis acids such as alkoxides, carboxylates and chelate compounds of titanium, zirconium, hafnium, tin, aluminum and zinc; boron trifluoride, boron trifluoride etherates; mineral acids such as sulfuric acid, phosphoric acid; sulfonic acids such as methanesulfonic acid and toluenesulfonic acid, and ionic fluids.

Suitably, the esterification catalyst is selected from alkoxides, carboxylates and chelate compounds of titanium, zirconium, hafnium, tin, aluminum and zinc. Suitable substances include tetraalkyl titanates such as tetramethyl titanate, tetraethyl titanate, tetra-n-propyl titanate, tetraisopropyl titanate, tetra-n-butyl titanate, tetraisobutyl titanate, tetra-sec-butyl titanate, tetraoctyl titanate, tetra(2-ethylhexyl) titanate; dialkyl titanates ($(RO)_2TiO$ in which R is, for example, isopropyl, n-butyl, isobutyl) such as isopropyl n-butyl titanate; titanium acetylacetonate chelates, such as diisopropoxybis(acetylacetonate)titanate, diisopropoxybis (ethylacetylacetonate)titanate, di-n-butylbis(acetylacetonate)titanate, di-n-butylbis(ethylacetoacetate)titanate, triisopropoxybis(acetylacetonate)titanate; zirconium tetraalkoxides such as zirconium tetraethoxide, zirconium tetrabutoxide, zirconium tetrabutyrate, zirconium tetrapropoxide, zirconium carboxylates such as zirconium diacetate; zirconium acetylacetonate chelates such as zirconium tetra(acetylacetonate), tributoxyzirconium acetylacetonate, dibutoxyzirconium bis(acetylacetonate); aluminum trisalkoxides such as aluminum triisopropoxide, aluminum trisbutoxide; aluminum acetylacetonate chelates such as aluminum tris(acetylacetonate) and aluminum tris(ethylacetylacetonate). More particularly, isopropyl n-butyl titanate, tetra(isopropyl) orthotitanate, tetra(butyl) orthotitanate, or the titanate- and/or zirconate-based branded products Tyzor® TnBT, Tyzor® TPT, Tyzor® 9000, Tyzor® BTM, Tyzor® BTP, Tyzor® DEA, Tyzor® ET, Tyzor® NPT, Tyzor® TiOT, Tyzor® TOT, Tyzor® TPT-20B, available from Dorf Ketal, or mixtures thereof are used.

Suitable ionic fluids (ionic liquids) are, for example, methylimidazoliumbutanesulfonic acid triflate and 1-ethyl-3-methylimidazolium hydrogensulfate.

The catalyst concentration depends on the type of catalyst. In the titanium compounds used with preference, it is 0.001 to 1.0 mol % based on the amount of terephthalic acid, especially from 0.01 to 0.2 mol %.

The reaction temperatures are between 100° C. and 250° C. The optimal temperatures depend on the feedstocks, progress of the reaction and catalyst concentration. They can be determined easily by experiments for each individual case. Higher temperatures increase the reaction rates and promote side reactions, for example olefin formation or formation of colored by-products. It is necessary for removal of the water of reaction that the alcohol can be distilled out of the reaction mixture. The desired temperature or the desired temperature range can be established via the pressure in the reactor. In the case of low-boiling alcohols, therefore, the reaction can be performed at elevated pressure, and in the case of higher-boiling alcohols under reduced pressure. For example, in the reaction of terephthalic acid with 2-ethylhexanol, a temperature range from 180° C. to 220° C. is employed within the pressure range from 300 mbar to 2 bar.

In a preferred embodiment of the process, the reaction pressure is reduced on attainment of a predetermined terephthalic acid conversion limit. The reduction in the pressure on attainment of a conversion limit can enable an essentially full conversion.

By reducing the pressure at constant temperature, the alcohol in the reactor is evaporated significantly more quickly than at the starting pressure. Preferably, the alcohol, after evaporation under reduced pressure, condensation, phase separation and collection of the alcohol in the lower region of the column, is not passed into the dispersing tank, but into a collecting tank for alcohol. In this way, the alcohol concentration in the reactor is reduced and the attainment of essentially full conversion is enabled.

For example, the conversion up to the conversion limit is conducted at 900 to 1100 mbar and then the pressure is reduced to below 900 mbar, for example 10 to 600 mbar, 100 to 550 mbar, especially 200 to 500 mbar. The conversion limit is generally greater than 90%, especially greater than 95%, for example about 97%. Appropriately, the pressure at the start of the conversion until the attainment of the conversion limit corresponds to ambient pressure, e.g. 1 atm.

The pressure is preferably reduced stepwise. More particularly, the pressure is reduced in steps of 20 to 50 mbar until the desired pressure level has been obtained. The stepwise reduction in pressure has the advantage that foaming of the reaction mixture, as is to be expected in the event of excessive rapid pressure reduction, is avoided.

For example, two successive pressure levels are established. The first pressure level is preferably in the range of 450 mbar to 550 mbar, for example about 500 mbar, and the second in the range of 150 to 350 mbar, for example about 300 mbar.

For example, the reaction of terephthalic acid with 2-ethylhexanol proceeds up to about 97% conversion at 1 atm; from 97% conversion, the pressure is reduced stepwise to about 500 mbar, such that full conversion is attained. In this case, a small reduction in the temperature in the reactor can be effected. In the case of a further reduction in pressure to about 300 mbar, optionally combined with an increase in the reactor temperature and/or an opposing inert gas stream, the stripping of the reaction mixture can be effected.

In a preferred embodiment, the process is conducted at a pressure of less than 900 mbar for 5% to 20% of reaction time, especially 8% to 12% of reaction time. For example, the conversion is conducted at a pressure of 250 to 550 mbar for about 10% of reaction time.

Appropriately, the reactor and dispersing tank will be operated at essentially the same pressure, especially about ambient pressure or else slightly negative pressure, such as about 900 mbar. Optionally, the reactor and dispersing tank can also be operated at different pressures.

Preference is given to performing the process according to the invention until the terephthalic acid has been essentially fully converted. The conversion can be determined via the determination of the acid number of the reaction suspension. The acid number is determined by neutralizing a sample of the reaction suspension with tetrabutylammonium hydroxide. The mass of tetrabutylammonium hydroxide consumed in the neutralization can be used to determine the molar amount of tetrabutylammonium hydroxide consumed, and stoichiometric considerations to determine the molar amount of free acid groups in unconverted terephthalic acid. Proceeding from the known molar amount of terephthalic acid used, it is thus possible to determine the conversion. Additional methods for determining the conversion are HPLC analyses and the measurement of the turbidity of the reaction suspension. In the process according to the invention, a conversion greater than 99% is preferably achieved.

After the reaction has ended, the reaction mixture consisting essentially of the desired ester and excess alcohol comprises, as well as the catalyst and/or conversion products thereof, small amounts of ester carboxylic acid(s) and/or unconverted carboxylic acid.

These crude ester mixtures are worked up by admixing the crude terephthalic diester with an aqueous base, evaporating water out of the mixture obtained, admixing the liquid phase obtained with water to form a water-in-oil emulsion, distilling water out of the emulsion and filtering the terephthalic diester.

First of all, the esterification catalyst is deactivated and precipitated by adding an aqueous base. At the same time, the acid and/or partial ester of the acid unconverted in the esterification reaction are converted to salts.

The aqueous base can be added in any suitable manner. It is preferably added beneath the liquid surface of the crude ester. Suitable apparatus for this purpose include, for example, probes and nozzles provided at one end of the vessel or the vessel walls. The mixture is then mixed vigorously, for example by means of a stirrer or circulation pump.

The amount of aqueous base added should be such that it is sufficient for complete neutralization of the acidic components of the crude ester. In practice, a greater or lesser excess of base is used. The total amount of the acidic components of the crude ester is appropriately detected via the acid number (in mg KOH/g). Preference is given to introducing 100% to 300% neutralization equivalents with the aqueous base, based on the acid number of the crude ester, especially 130% to 220%. A neutralization equivalent is understood to mean the amount of base that can bind the same number of protons as 1 mg of KOH. In other words, an excess of base of up to 400% is used, preferably 100% to 300%.

Preferably, the reactor is actively cooled, for example to a temperature between 100 and 150° C., for example 135 to 145° C. before the addition and also through the addition of the aqueous base. Preferably, the aqueous base is also cooled before the addition, for example to a temperature of 10 to 40° C. The metered addition of cold alkali can additionally cool the reactor. This is especially appropriate in order to reduce or optionally to completely prevent the evaporation of water on addition of the aqueous base.

Useful aqueous bases include solutions of hydroxides, carbonates, hydrogencarbonates of alkali metals and alkaline earth metals. Aqueous alkali metal hydroxide solutions are generally preferred. Aqueous sodium hydroxide solution is particularly preferred because of its ease of availability.

The concentration of the aqueous base is not critical per se, but there may be hydrolysis of the esters at the site of introduction of the base when concentrated alkali solutions are used. On the other hand, the concentration of the aqueous base should not be too low, since the water introduced with the aqueous base has to be removed again in the subsequent step. Therefore, preference is given to aqueous bases of moderate to low concentration, for example those of a concentration of 0.5% to 25% by weight, especially 1% to 10% by weight. Aqueous sodium hydroxide solution having a concentration of 1% to 5% by weight is particularly preferred.

Often, the precipitated solid consisting essentially of catalyst breakdown products and salts of unconverted acid or partial esters of polybasic acids is present in finely divided form and is difficult to filter. Appropriately, the fine particles are agglomerated to larger, readily removable particles. For this purpose, the liquid phase is admixed with water to form a water-in-oil emulsion. The water is distributed as a disperse phase in the form of fine droplets in the liquid organic phase. The fine solid particles migrate to the interface between water droplets and surrounding organic phase. In the course of the subsequent evaporation of the water, the fine particles agglomerate and form coarse, efficiently removable particles.

In order that a separate water phase forms, the amount of water added must be greater than that corresponding to the solubility of water in the organic phase. One factor on which the water solubility in the organic phase depends is the content of unconverted alcohol, since the alcohol acts as a solubilizer. The higher the alcohol content, the more water has to be added to form an emulsion. In the case of residual alcohol contents of 1% to 10% by weight, suitable amounts are generally from 10 to 80 g of water, preferably 30 to 50 g, based on 1 kg of crude ester, especially about 5% by weight of water.

The water phase is divided into fine droplets with a suitable stirrer or homogenizer, or by pumped circulation of the emulsion using a circulation pump. The water droplets produced preferably have a mean droplet size of less than 1000 µm. Examples of suitable stirrers having a high specific stirrer input are disk stirrers. Alternatively, particularly in the case of a continuous process regime, it is possible to use a mixing nozzle in which water is added directly to the crude ester stream via a dispersing valve.

The emulsion is appropriately formed at about standard pressure.

The water in the emulsion thus produced is distilled off again in the next step.

After this treatment, the solids are in efficiently filterable form; no fines fraction passes through in the filtration. Suitable filters for filtration of the ester are all suitable filters such as chamber filter presses, belt filters, cartridge filters or pan filters. For a continuous process regime, pan filters with centrifugal cake ejection are particularly suitable. The solids removed are discarded.

After the filtration, the ester can be subjected to various aftertreatments, such as a steam stripping or the like. A steam stripping may additionally be followed by a further aftertreatment step, for example a filtration or treatment with activated carbon, in which the product, after the steam stripping, at a temperature of, for example, 20 to 100° C., is admixed with activated carbon (for example 0.1% to 10% by weight) and stirred for a period of, for example, 1 to 120 min. The activated carbon-treated product is then typically subjected to a filtration step.

The invention further relates to an apparatus for preparation of terephthalic diesters by the process described above, comprising a dispersing tank connected to a reactor in a fluid-conducting manner, the reactor contents being pumpable through a heat exchanger, a column connected to the reactor in a vapor-conducting manner, and a condenser connected to the column in a vapor-conducting manner and to a phase separator in a liquid-conducting manner, the phase separator being connected to the column in a liquid-conducting manner in order to pass collected organic phase into the column, a collecting tray in the lower region of the column and a collecting vessel connected to the collecting tray and the dispersing tank in a fluid-conducting manner.

The invention is illustrated in detail by the appended FIGURE and the example which follows.

FIG. 1 shows a plant suitable for performing the process according to the invention.

According to FIG. 1, terephthalic acid from the reservoir 10 is metered into a dispersing tank 7 and mixed in alcohol to form a preliminary suspension using a stirrer 11. Initially, alcohol from the reservoir 9 is metered via the collecting tank 13 and the pump 14 into the dispersing tank 7; during the reaction, return alcohol from the collecting tray 12 of the column 6 is passed into the collecting tank 13. The alcohol is drawn off from the collecting tank 13 by means of the pump 14 and passed into the dispersing tank 7 as required. The preliminary suspension is passed into the upper region of the reactor 1 with the aid of a pump 8. Within the reactor 1 are a further portion of the alcohol and the esterification catalyst. At the lowest point in the reactor 1, the reaction suspension is drawn off from the reactor using a pump 2 outside the reactor and conducted through a heat exchanger 3 outside the reactor. The reaction suspension heated in the heat exchanger 3 is recycled back into the reactor 1 in the upper region thereof. The vapor passes through the column 6 and is at least partly condensed in the condenser 4. In the phase separator 5, the condensate is separated into an aqueous phase and an organic phase. The aqueous phase is discarded, the organic phase is conducted through column 6, and the descending condensate is collected on a collecting tray 12 and passed into the dispersing tank 7.

EXAMPLE 1

The example which follows illustrates the preparation of dioctyl terephthalate (DOTP) by reaction of terephthalic acid with 2-ethylhexanol in a Miniplant system. One embodiment of the process of the invention is arrived at when the system is supplemented with a dispersing tank in which the terephthalic acid is slurried in alcohol, and the terephthalic acid suspension is passed into the reactor from the dispersing tank in a distribution over time. The alcohol used is dewatered organic phase from a preceding experiment, which is collected on a collecting tray in the lower region of the distillation column and led off.

The reactions were conducted in an oil-heated 1.6 L jacketed reactor having a three-level crossbeam stirrer, 25 cm distillation column having 4-6 theoretical plates (5×Montz A3-1000), condenser, Anschütz-Thiele adapter, phase separation vessel for separating out the aqueous component of the condensed vapors, collecting vessel for the water separated out, pump for recycling the organic component of the condensed vapors from the phase separation vessel to the top of the distillation column, nitrogen inlet tube, vacuum connection with corresponding membrane vacuum pump and outlet valve for removal of the 2-ethylhexanol excess after attainment of the target conversion.

The above-described apparatus was initially charged with 2-ethylhexanol (977 g, 7.50 mol) under a nitrogen atmosphere, and terephthalic acid (415 g, 2.50 mol) was added while stirring (250 rpm). The slurry thus obtained was heated to 170° C. while stirring under atmospheric pressure and Tyzor TPT 20 B (mixture of organic alkoxytitanates; Dorf Ketal, 0.68 g, 2.31 mmol) was added, and then the release of water commenced as a result of the onset of esterification reaction. During the reaction, the temperature of the heating bath was automatically regulated by the thermostat in such a way that the temperature of the reaction mixture during the esterification was about 25° C. below that of the heating bath. The vapors obtained at the top of the distillation column were condensed and transferred into the phase separation vessel, and a water-rich phase settled out at the base of the vessel and was transferred continuously via a siphon to a collecting vessel and was thus removed from the system, and a water-saturated organic phase flowed out of the upper region of the separation vessel. The organic phase thus obtained was recycled by means of a pump to the top of the distillation column and dewatered in the distillation column by rectification. The dewatered organic phase ran from the lower end of the distillation column back into the reactor.

On attainment of >90% conversion (determined by quantitative HPLC measurement; after about 7 h), the pressure was reduced stepwise from atmospheric pressure to 500 mbar and a portion of the 2-ethylhexanol excess was removed from the system. After the attainment of full conversion (no terephthalic acid visible in the HPLC measurements, clear solution), the pressure was reduced to 300 mbar and 2-ethylhexanol was removed by distillation from the system. In the course of this, 2-ethylhexanol was collected on a collecting tray in the lower region of the column and led off. After about 9.25 h, the reaction and removal of the 2-ethylhexanol excess were complete.

The acid number of the crude product thus obtained (~95% DOTP, ~5% 2-ethylhexanol) was determined by means of automatic titration (0.07 mg KOH/g) and a 2.0% by weight solution of NaOH in water (8.20 g, i.e. 200% excess based on the amount necessary in stoichiometric terms, determined via titration) was added while stirring (250 rpm) at 100° C. under a nitrogen atmosphere. The resultant solution was stirred for 15 min and the water present was removed under reduced pressure. Subsequently, a further amount of water (54 g) was added at 100° C. and the resultant emulsion was stirred (260 rpm) under a nitrogen atmosphere for 20 min, and then the water present was removed by distillation (100° C., 300 mbar). The deactivated catalyst was thus converted to an easily removable solid which was removed by pressure filtration through a filter plate (Seitz pressure suction filter, KS 100 filter plate, 2 bar abs).

The excess 2-ethylhexanol was removed from the clear catalyst-free crude product solution thus obtained by steam distillation (1 bar steam, still temperature 150-200° C., 1.17 h, atmospheric pressure) while stirring (250 rpm) in a nitrogen atmosphere, which gave pure DOTP.

Excess 2-ethylhexanol which was obtained during the reaction by distillative removal from the reaction system and during the steam distillation was collected, combined and used as starting material in the subsequent batch, which was conducted under the same conditions as described above. Overall, under the conditions specified, a series of five batches was conducted with reuse of excess 2-ethylhexanol.

The results are summarized in table 1. The yield of DOTP in all experiments was >98.3% of theory, and the product had a high purity (color number generally <20 Hazen (APHA); ester content (GC area %)>99.8; acid number<0.05 mgKOH/g). The 2-ethylhexanol reused comprised only a small amount of impurities, which did not lead to a deterioration in the product in the subsequent batches.

TABLE 1

| Batch no. | Reuse from batch no. | Acid number of pure DOTP/mgKOH/g | Color number of pure DOTP/ Hazen (APHA) | Purity of DOTP (diester content)/ GC area % | Yield of DOTP/ % of theory |
|---|---|---|---|---|---|
| 1 | fresh | 0.02 | 27 | 99.80 | 98.90 |
| 2 | 1 | 0.04 | 18 | 99.80 | 98.30 |
| 3 | 2 | 0.03 | 16 | 99.92 | 99.60 |
| 4 | 3 | 0.04 | 17 | 99.92 | 99.90 |
| 5 | 4 | 0.01 | 16 | 99.88 | 99.85 |

| Batch no. | Low boilers present in the excess of 2-EH/ GC area % | Medium boilers present in the excess of 2-EH/GC area % | 2-EH content of the excess 2-EH/ GC area % | DOTP present in the excess of 2-EH/ GC area % | High boilers present in the excess of 2-EH/ GC area % |
|---|---|---|---|---|---|
| 1 | 0.19 | 0.11 | 98.88 | 0.82 | 0.00 |
| 2 | 0.37 | 0.07 | 98.79 | 0.77 | 0.00 |

TABLE 1-continued

| | | | | | |
|---|---|---|---|---|---|
| 3 | 0.38 | 0.14 | 98.96 | 0.52 | 0.00 |
| 4 | 0.44 | 0.12 | 98.82 | 0.62 | 0.00 |
| 5 | 0.52 | 0.13 | 98.86 | 0.49 | 0.00 |

The invention claimed is:

1. A process for preparing a terephthalic diester which comprises reacting terephthalic acid with at least one alcohol, wherein
   a) suspending terephthalic acid in the alcohol in a dispersing tank to obtain a preliminary suspension,
   b) passing the preliminary suspension from the dispersing tank into a reactor and converting in the presence of an esterification catalyst, and
   c) distilling of water of reaction together with vapor as alcohol-water azeotrope, the vapor is at least partly condensed, the condensate is separated into an aqueous phase and an organic phase and the organic phase is conducted through a column in which the organic phase is run counter to at least a portion of the vapor, and the organic phase is collected in the lower region of the column and at least partly passed into the dispersing tank and/or intermediately stored in a collecting vessel and passed out of the collecting vessel into the dispersing tank for same batch or a subsequent batch.

2. The process according to claim 1, wherein the organic phase passed into the dispersing tank has a water content lower than the solubility of water in the alcohol.

3. The process according to claim 1, wherein the organic phase passed into the dispersing tank has a water content of less than 3% by weight.

4. The process according to claim 1, wherein
   b1) the reactor is initially charged with a mixture of alcohol and catalyst having a temperature at or above the boiling temperature of the alcohol and at or above the minimum reaction temperature, and
   b2) the preliminary suspension is metered into the reactor.

5. The process according to claim 4, wherein the reaction rate is controlled via the rate of metered addition of the preliminary suspension.

6. The process according to claim 4, wherein the initially charged mixture of alcohol and catalyst is heated with maximum energy input, and the energy input is not throttled on commencement of the metered addition of the preliminary suspension.

7. The process according to claim 1, wherein the preliminary suspension is metered into the reactor at a temperature of 50 to 150 °C.

8. The process according to claim 1, wherein the reaction pressure is reduced on attainment of a predetermined terephthalic acid conversion limit.

9. The process according to claim 8, wherein the conversion limit is greater than 90%.

10. The process according to claim 8, wherein the reaction pressure is reduced stepwise on attainment of the terephthalic acid conversion limit.

11. The process according to claim 8, which is conducted at a pressure of less than 900 mbar for 5% to 20% of the reaction time.

12. The process according to claim 1, wherein the esterification catalyst is selected from the group consisting of a Lewis acid, mineral acid, sulfonic acid and an ionic fluid.

13. The process according to claim 1, wherein the esterification catalyst is selected from the group consisting of alkoxide, carboxylate or chelate compounds of titanium, zirconium, hafnium, tin, aluminum or zinc; boron trifluoride; boron trifluoride etherates; sulfuric acid;
   phosphoric acid; and methanesulfonic acid or toluenesulfonic acid.

14. The process according to claim 1, wherein the esterification catalyst is selected from the group consisting of acidic ion exchangers; zeolites; oxides of magnesium, aluminum, zinc, titanium, silicon, tin, lead, antimony, bismuth, molybdenum or manganese; and hydroxides of magnesium, aluminum, zinc, titanium. silicon, tin, lead, antimony, bismuth, molybdenum or manganese.

15. The process according to claim 1, wherein the esterification catalyst is soluble in the alcohol.

16. The process according to claim 1, wherein the alcohol is alcohol selected from the group consisting of a linear aliphatic $C_4$-$C_{18}$ alcohol, a branched aliphatic $C_4$-$C_{18}$ alcohol, cyclic aliphatic $C_4$-$C_{18}$ alcohol and an aromatic alcohol.

17. The process according to claim 1, which is performed continuously or batchwise.

18. The process according to claim 1, wherein the reaction in the reactor is conducted at a temperature of 100 to 250° C.

19. The process according to claim 1, wherein the alcohol is used in such a stoichiometric excess that the crude esterification product comprises 15% to 35% by weight of alcohol at theoretical full conversion.

20. The process according to claim 1, wherein an inert gas is metered into the reactor and/or a stream of the reaction suspension for fluidization.

21. The process according to claim 20, wherein the inert gas is metered in an amount of 0.01 to 5 units by volume of the inert gas per unit volume of the reaction suspension per hour.

22. The process according to claim 1, wherein the crude terephthalic diester is worked up by admixing with an aqueous base, evaporating water out of the mixture obtained, admixing the liquid phase obtained with water to form a water-in-oil emulsion, distilling water out of the emulsion and filtering the terephthalic diester.

23. The process according to claim 1, wherein the reaction suspension is heated by being pumped in circulation through a heat exchanger.

* * * * *